United States Patent [19]

Coburn et al.

[11] Patent Number: 5,274,091

[45] Date of Patent: Dec. 28, 1993

[54] ADMPT AND ITS SYNTHESIS

[75] Inventors: Michael D. Coburn; Donald G. Ott, both of Los Alamos, N. Mex.

[73] Assignee: The United States of America as represented by the United States Department of Energy, Washington, D.C.

[21] Appl. No.: 980,888

[22] Filed: Nov. 24, 1992

[51] Int. Cl.⁵ .................................. C07D 257/08
[52] U.S. Cl. ........................................... 544/179
[58] Field of Search .................................. 544/179

[56] References Cited

PUBLICATIONS

Michael D. Coburn et al., "An Improved Synthesis of 3,6–Diamino-1,2,4,5-Tetrazine. I," J. Heterocyclic Chem., 27, pp. 1941-1945 (1990).
M. D. Coburn et al., "An Improved Synthesis of 3,6–Diamino-1,2,4,5-Tetrazine. II From Triaminoguanidine and 2,4–Pentanedione," J. Heterocyclic Chem., 28, pp. 2049-2050 (1991).
Chao-Han Lin et al., "The Synthesis of sym–Diaminotetrazine," J. Am. Chem. Soc., 76, pp. 427-430 (1954).
R. N. Butler et al., "Sequential Attach By A Diketone On A Polyhydrazine; The Reaction Of Triaminoguanidine With Acetylacetone," J. Chem. Soc., (C), pp. 2510-2512 (1970).

*Primary Examiner*—John M. Ford
*Attorney, Agent, or Firm*—Richard J. Cordovano; Paul D. Gaetjens; William R. Moser

[57] ABSTRACT

3-Amino-6-(3,5-dimethylpyrazol-1-yl)-1,2,4,5-tetrazine (ADMPT) and a method of making it.

8 Claims, 1 Drawing Sheet

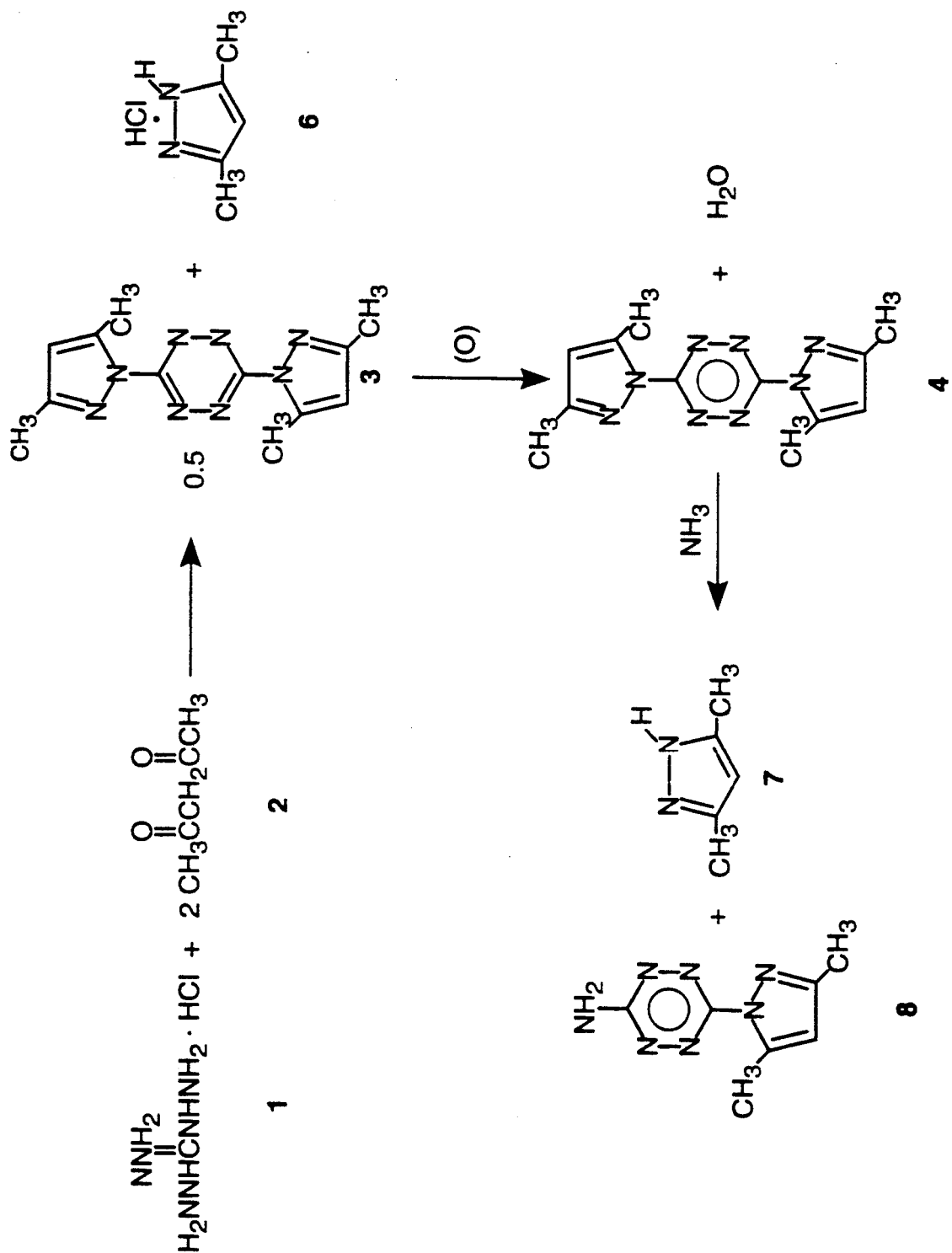

ADMPT AND ITS SYNTHESIS

BACKGROUND OF THE INVENTION

This invention is the result of a contract with the Department of Energy (Contract No. W-7405-ENG-36).

3-Amino-6-(3,5-dimethylpyrazol-1-yl)-1,2,4,5-tetrazine (compound 8, ADMPT) is useful as a precursor to compounds having antibiotic, herbicidal, fungicidal, and insecticidal properties. For example, it may be reacted with N,N-dimethylethylenediamine ($CH_3CH_3NCH_2CH_2NH_2$) to form 3-amino-6-(dimethylaminoethylamino)-1,2,4,5-tetrazine ($C_2N_4NH_2NHCH_2CH_2NCH_3CH_3$), which is expected to possess antibiotic properties, as may be seen from United Kingdom patent GB 1245443, dated Sept. 8, 1971. The inventive compound may be reacted with disubstituted amines ($R_1R_2NH$) to form diamino tetrazines having various alkyl group substituents on one of the amino nitrogens, which are expected to possess biocidal properties, as may be seen from the German Offenlegungsschrift patent DE 3508214 A1.

SUMMARY OF THE INVENTION

This invention is 3-amino-6-(3,5-dimethylpyrazol-1-yl)-1,2,4,5-tetrazine (compound 8, ADMPT) and a method of making it. Triaminoguanidine monohydrochloride (compound 1) in water solution is combined with 2,4-pentanedione (compound 2) to form a precipitate comprised of 3,6-bis(3,5-dimethylpyrazol-1-yl)-1,2-dihydro-1,2,4,5-tetrazine (compound 3). A mixture of compound 3 in a suitable solvent is contacted with nitric oxide (NO) or nitrogen dioxide ($NO_2$) to form 3,6-bis(3,5-dimethylpyrazol-1-yl)-1,2-dihydro-1,2,4,5-tetrazine (compound 4). The NO or $NO_2$ is then removed from the mixture by passing an inert gas through the mixture or, alternatively, compound 4 is separated from the mixture and mixed with fresh solvent to form a mixture free of NO and $NO_2$. The mixture is contacted with ammonia ($NH_3$) at a temperature less than about 35 C. to form compound 8 and 3,5-dimethyl-1H-pyrazole (compound 7). A preferred solvent for the oxidation is 1-methyl-2-pyrrolidinone (NMP) and for the ammonolysis is toluene.

SUMMARY OF THE DRAWING

The Drawing depicts a sequence of chemical reactions, using structural formulas, which is believed to occur when carrying out the steps of the invention. The compound numbers are correlated with compound names in the above paragraph.

DETAILED DESCRIPTION OF THE INVENTION

There are several methods which may be used by one skilled in the art to synthesize compound 1. Following is an example of the method used by the present inventor.

EXAMPLE 1

34.1 g of hydrazine monohydrate was added to a slurry consisting of 19.1 g of guanidine hydrochloride in 100 ml of 1,4-dioxane. The mixture was stirred and heated to a temperature of about the boiling point of 1,4-dioxane for about 2 hours, using a reflux condenser to prevent loss of material. Then, the mixture was allowed to cool and filtered. The solid material from the filtration step was washed with 1,4-dioxane, dried, and identified as 27.7 g of pure compound 1.

Other suitable organic solvents, such as 1-propanol, may be used in place of 1,4-dioxane. When water was used as the solvent, the yield of compound 1 was poor. The reactants were purchased from the Aldrich Chemical Company.

Compound 3 was made in the manner illustrated by the following example.

EXAMPLE 2

10.0 g of compound 2 was added in a dropwise manner to a solution consisting of 7.03 g of compound 1 in 50 ml of water at room temperature. The temperature of the mixture rose during addition of compound 2. The amount of compound 2 added was the stoichiometric amount needed to completely react with compound 1. The mixture was stirred for about 0.5 hours and then heated and stirred at 70 C. for about 4 hours, during which time a solid precipitated from the solution. The solid was filtered from the mixture after the mixture cooled, washed with water, dried, and identified as 5.77 g of pure compound 3. The yield was 85%.

The conditions of Example 2 are believed to be optimum. The reaction will take place slowly at room temperature and yields appear to be less at temperatures above 70 C. The reaction was run in 1-propanol, in which compound 2 is slightly soluble, but yields were not as large as when water was used as the reaction medium. Yield when using 1-propanol was increased by adding a small amount of water to the reaction mixture. A one pot process may be used to make compounds 1 and 3. Solvent is distilled off from the mixture of solvent and compound 1, then water is added, and then compound 2 is added.

Oxidation of compound 3 to compound 4 using gaseous oxygen in 1,4-dioxane, in sulfolane, in 1,2-dichloroethane, and in NMP was investigated. At room temperature, the reaction was found to be faster in NMP than in the other solvents, but was still very slow. At 90 C. in NMP using $O_2$, the reaction was complete in 0.5 hour, but significant amounts of by-products were formed. These by-products were also found in lesser amounts in the reactions run at room temperature.

NO and $NO_2$ were found to be effective in converting compound 3 to compound 4. A gas may be bubbled through a mixture of compound 3 in a suitable solvent or the NO or $NO_2$ may be contacted with the mixture in a pressure reactor. For example, a 0.5 molar mixture of compound 3 in NMP was placed in a pressure reactor with an excess of NO above it at 50 psig for 1 hour at room temperature, resulting in complete conversion to compound 4 with no trace of by-products. 70% conversion to compound 4 was obtained when a 1.0 molar slurry of compound 3 was contacted with an equimolar amount of $NO_2$. Complete conversion was obtained when 2 molar equivalents of $NO_2$ were used. A suitable solvent is an organic solvent in which compound 3 is at least slightly soluble and which does not react with the components of the mixture. A substance which is slightly soluble in a solvent will generally have a solubility of at least about one gram per liter of solvent. Examples of suitable solvents are NMP, toluene, formamide, and dimethylformamide. NMP is a preferred solvent. Following are illustrative examples.

EXAMPLE 3

A slurry consisting of 6.8 g of compound 3 and 50 ml of NMP at room temperature was placed in a gas washing bottle having a glass frit gas dispersion tube at its bottom. Nitric oxide in gaseous form from a storage cylinder was passed into the slurry through the dispersion tube at a rate of 500 ml/minute for 1 hour. Then the mixture was poured into 200 ml of ice water and the resulting mixture filtered to isolate a red solid. The solid was washed with water, dried, and identified as 6.7 g of pure compound 4. The yield was 99%.

EXAMPLE 4

A slurry consisting of 13.6 g of compound 3 and 50 ml of NMP at room temperature was placed in a gas washing bottle having an open-ended gas dispersion tube extending to its bottom. $NO_2$ in gaseous form was passed into the rapidly-stirred slurry through the tube. The gas could not be passed into the slurry by means of glass frit due to plugging of the frit. 3.2 ml of liquid $NO_2$ was vaporized and contacted with the slurry in a period of 5 or 10 minutes. Pure compound 4 in an amount of 13.3 g was then separated from the mixture. The yield was 99%.

Compound 4 is converted to compound 8 and 3,5-dimethyl-1H-pyrazole (compound 7) by ammonolysis. The reaction is carried out by contacting gaseous ammonia with a mixture of compound 4 and a suitable solvent, such as toluene (which is preferred), NMP, dimethylformamide, or formamide. $NH_3$ may be bubbled through the mixture or added to a pressure reactor containing the mixture. Compound 4 must be at least slightly soluble in the solvent and the solvent must not react with the components of the mixture. In general, chlorinated solvents, esters, and ketones will not be suitable, as they will react with $NH_3$. The ammonolysis proceeds rapidly at room temperature. When ammonolysis is carried out at higher temperatures, a number of other compounds, including 3,6-diamino-1,2,4,5-tetrazine (compound 5), are formed. It is believed that a temperature below about 35 C. is required for the ammonolysis of compound 4 to compound 8 to be significantly favored over other reactions of compound 4 with $NH_3$ and that ammonolysis to compound 8 will proceed with reasonable rapidity at temperatures in the area of 0 C. When a compound 4 and solvent mixture is contacted with $NH_3$ at a temperature below 35 C. and then at a temperature above about 50 C., most of the compound 4 will be converted to compound 5. Those skilled in the art will appreciate the interplay of time and temperature in regard to the relative amounts of compounds 5 and 8 which are formed. In synthesizing compound 5, it is desirable that $NH_3$ be present in an amount greater than the stoichiometric requirement, since the reaction kinetics are such that the ammonolysis takes place slowly when only stoichiometric amounts are present. However, ammonolysis to compound 8 takes place rapidly without an excess of $NH_3$. Following are illustrative examples.

EXAMPLE 5

A mixture consisting of 13.6 g of compound 4 and 250 ml of toluene at room temperature was placed in a gas washing bottle having a glass frit gas dispersion tube at its bottom. $NH_3$ from a storage cylinder was passed into the mixture through the dispersion tube at a rate of 60 ml/minute for 0.5 hour. A precipitate formed and the mixture was filtered to isolate the solid. The solid was washed with toluene, dried, and identified as 9.5 g of pure compound 8. The yield was 99%.

EXAMPLE 6

A 100 ml capacity pressure reactor was charged with a mixture of 2.7 g of compound 4 and 50 ml of toluene at room temperature. 0.6 g of $NH_3$ gas from a storage cylinder was added to the space above the mixture over a period of about 15 minutes with no heating. After $NH_3$ addition, the pressure in the reactor was about 60 psig. As the reaction took place, the pressure dropped and stabilized at about 30 psig. After 3 hours, with stirring by the magnetic stirrer with which the reactor was equipped, the vessel was vented and the brick-red precipitate was separated by filtration, washed with toluene, and dried. The weight of the dry precipitate was 1.7 g and it was 98 mol% compound 8 with the balance being compound 4. No compound 5 was detected in the precipitate. The small amount of compound 4 could be removed by recrystallization of the precipitate from 1,4-dioxane.

Oxidation and ammonolysis may be accomplished without isolating compound 4 from the solvent containing compound 4 and NO or $NO_2$ if the gas used for oxidation is removed from the reaction mixture before addition of ammonia. This may be done by purging with a gas which is inert with respect to the reaction mixture, such as air or nitrogen.

Compounds were identified by means of carbon-13 and nitrogen-15 nuclear magnetic resonance spectroscopy and elemental (combustion) analysis.

This invention is described in a paper entitled "An Improved Synthesis of 3,6-Diamino-1,2,4,5-tetrazine", which appeared in the Journal of Heterocyclic Chemistry, vol. 28, page 2049 (Dec. 1991). This paper is incorporated in full into this patent application.

The above examples are intended to be illustrative only and are not intended to constitute an undue limitation on the broad scope of the claims. Modifications and variations will be apparent to those skilled in the art.

We claim:

1. The compound 3-amino-6-(3,5-dimethylpyrazol-1-yl)-1,2,4,5-tetrazine.

2. A process for making 3-Amino-6-(3,5-dimethylpyrazol-1-yl)-1,2,4,5-tetrazine which comprises:
   a. combining a solution of triaminoguanidine monohydrochloride in water with 2,4-pentanedione to form a precipitate and recovering said precipitate;
   b. forming a first mixture of the precipitate and a suitable solvent;
   c. contacting said first mixture with nitric oxide or nitrogen dioxide;
   d. separating a solid fraction from said first mixture and mixing said solid fraction with a suitable solvent to form a second mixture;
   e. contacting said second mixture with ammonia at a temperature below about 35 C.; and
   f. recovering 3-amino-6-(3,5-dimethylpyrazol-1-yl)-1,2,4,5-tetrazine from the second mixture.

3. The process of claim 2 where said triaminoguanidine monohydrochloride is synthesized by reacting guanidine hydrochloride and hydrazine monohydrate in a non-aqueous liquid.

4. The process of claim 2 where said solvent in step b is 1-methyl-2-pyrrolidinone and said solvent in step d is toluene;

5. A process for making 3-Amino-6-(3,5-dimethylpyrazol-1-yl)-1,2,4,5-tetrazine which comprises:
  a. combining a solution of triaminoguanidine monohydrochloride in water with 2,4-pentanedione to form a precipitate and recovering said precipitate;
  b. forming a mixture of the precipitate and a suitable solvent;
  c. contacting said mixture with nitric oxide or nitrogen dioxide;
  d. passing an inert gas through the mixture to remove said nitric oxide or said nitrogen dioxide;
  e. contacting the mixture with ammonia at temperature below about 35 C.; and
  f. recovering 3-Amino-6-(3,5-dimethylpyrazol-1-yl)-1,2,4,5-tetrazine from the mixture.

6. The process of claim 5 where said triaminoguanidine monohydrochloride is synthesized by reacting guanidine hydrochloride and hydrazine monohydrate in a non-aqueous liquid.

7. The process of claim 5 where said solvent is 1-methyl-2-pyrrolidinone.

8. The process of claim 5 where said solvent is toluene.

* * * * *